United States Patent [19]

Lezdey et al.

[11] Patent Number: 5,492,889
[45] Date of Patent: Feb. 20, 1996

[54] TREATMENT OF MAST CELL TUMORS

[76] Inventors: John Lezdey, 976 Kingston Dr., Cherry Hill, N.J. 08034; Allan Wachter, 9822 S. Grandview, Tempe, Ariz. 85284

[21] Appl. No.: 331,022

[22] Filed: Oct. 17, 1994

Related U.S. Application Data

[63] Continuation-in-part of Ser. No. 122,204, Sep. 15, 1993, Pat. No. 5,376,633, which is a continuation-in-part of Ser. No. 953,234, Sep. 29, 1992, abandoned.

[51] Int. Cl.$^6$ ........................................................ A61K 38/16
[52] U.S. Cl. ........................ 514/8; 514/12; 514/21; 530/380; 530/392; 530/397
[58] Field of Search .................................. 514/8, 12, 21; 530/380, 392, 397

[56] References Cited

U.S. PATENT DOCUMENTS

| | | | |
|---|---|---|---|
| 5,093,316 | 3/1992 | Lezdey et al. | 514/8 |
| 5,114,917 | 5/1992 | Lezdey et al. | 514/8 |
| 5,134,119 | 6/1992 | Lezdey et al. | 514/8 |
| 5,166,134 | 11/1992 | Lezdey et al. | 514/8 |
| 5,190,917 | 3/1993 | Lezdey et al. | 514/12 |
| 5,215,965 | 6/1993 | Lezdey et al. | 514/12 |
| 5,217,951 | 6/1993 | Lezdey et al. | 514/8 |
| 5,290,762 | 3/1994 | Lezdey et al. | 514/8 |
| 5,346,886 | 9/1994 | Lezdey et al. | 514/8 |

OTHER PUBLICATIONS

Gomez et al, *Biological Abstracts,* vol. 79 (7), Ref. #60215, 1984 (Arch. Invest. Med. 15(2), 173–181, 1984).

Courtney et al, *Nature,* vol. 313, pp. 149–151, Jan., 10, 1985.

Wachter et al, *Ann. Allergy,* vol. 69, No. 5, pp. 407–414, Nov. 1992.

*Primary Examiner*—Howard E. Schain
*Assistant Examiner*—Abdel A. Mohamed
*Attorney, Agent, or Firm*—John Lezdey

[57] ABSTRACT

There is provided a method for treating tumors in mammals by the administration of alpha 1-antitrypsin alone or in combination with other protease inhibitors.

6 Claims, No Drawings

TREATMENT OF MAST CELL TUMORS

RELATED APPLICATIONS

This application is a continuation-in-part of application Ser. No. 08/122,204 filed Sep. 15, 1993, now U.S. Pat. No. 5,376,633 entitled "Antiviral Agents" of, Lezdey et al, which is a continuation-in-part of application Ser. No. 07/953,234 filed Sep. 29, 1992, now abandoned.

FIELD OF THE INVENTION

The present invention relates to the treatment of tumors in mammals. More particularly, the present invention relates to the treatment of tumors in mammals., especially mast cell tumors, utilizing a serine protease inhibitor which is capable of binding with the tumor and/or binding with cells which are an underlying cause of the tumor.

BACKGROUND OF THE INVENTION

The role of mast cells in humans is the same as in animals. In addition, animals contain counterparts to human $\alpha$-1-antichymotrypsin, $\alpha$-1-antitrypsin and other serine protease inhibitors. In fact, it has been shown that human $\alpha$-1-antitrypsin will bind with animal mast cell mediators.

It has been reported by Froll et al in *Carcinogenesis*, Vol. 2. Mechanism of Tumor Promotion and Carcinogenesis, New York, Raven; (1978) p. 301–312, that cancer cells secrete elevated amounts of proteolytic enzymes, including serine proteases, at the earliest steps in carcinogenesis, and that intracellular levels of $\alpha$-1-antitrypsin ($\alpha$1-PI), as well as extracellular milieu of tumors are increase. However, the proteolytic activities of the aggressive cancer-associated proteases are not efficiently inhibited.

It is also known that a cancer cell alone endowed with a latent gene DNA code for a peptide secreted by cancer cells which is introduced by a virus as a protooncogene remains suppressed until activated by a cancer proliferation promoting agent which also triggers the synthesis of cancer-associated serine proteases. Viruses such as hepatitis virus and herpes virus are the most common viruses which promote cancer cell activity.

Alpha 1-antichymotrypsin is a plasma protease inhibitor synthesized in the liver. It is a single glycopeptide chain of approximately 68,000 daltons and belongs to a class of serine protease inhibitors with an apparent affinity toward chymotrypsinlike enzymes.

Alpha 2-macroglobulin is a glycoprotein containing 8–11% carbohydrate which can be isolated from plasma by gel filtration chromatography.

Alpha 1-proteinase inhibitor (alpha 1-antitrypsin) is a glycoprotein having a molecular weight of 53,000 determined by sedimentation equilibrium centrifugation. The glycoprotein consists of a single polypeptide chain to which several oligosaccharide units are covalently bonded. Human alpha 1-proteinase inhibitor has a role in controlling tissue destruction by endogenous serine proteinases. A genetic deficiency of alpha 1-proteinase inhibitor, which accounts for 90% of the trypsin inhibitory capacity in blood plasma, has been shown to be associated with the premature development of pulmonary emphysema. The degradation of elastin associated with emphysema probably results from a local imbalance of elastolytic enzymes and the naturally occurring tissue and plasma proteinase inhibitors. Alpha-1-proteinase inhibitor inhibits human pancreatic and leukocyte elastases. See Pannell et al, Biochemistry. 13, 5339 (1974); Johnson et al, Biochem. Biophys. Res. Commun., 72 33 (1976); Del Mar et al, Biochem. Biophys. Res. Commun., 88, 346 (1979); and Heimburger et al, Proc, Int. Res. Conf. Proteinase Inhibitors. 1st, 1–21 (1970).

It is understood that the term "serine protease inhibitors" as used herein refers to the inhibitors derived from a particular species and inhibits the proteases of the same species. However, human serine protease inhibitors may be used in veterinary products but not visa versa.

SUMMARY OF THE INVENTION

The invention comprises treating tumors in mammals by administering to the mammal in need of treatment an effective amount of alpha 1-antitrypsin alone or in combination with other serine protease inhibitors and/or asteroid.

The invention is especially useful in the treatment of mast cell tumors and virally derived tumors.

DESCRIPTION OF THE PREFERRED EMBODIMENT

Alpha 1-antitrypsin ($\alpha$1-PI) is a serine protease inhibitor which is involved in the control of many intra- and extracellular physiological processes including degradative actions in cancer cell invasion, metastatic spread and neovascularization of tumors. $\alpha$1-PI also binds with proteases which are involved in the proliferation of cancer cells as well as cancer cells to prevent the formation of cancer cell-protease complexes.

Cancer cells produce peptides which are homologous to the enzyme binding sites of $\alpha$1-PI. These peptides are capable of binding with proteases in a manner whereby $\alpha$1-PI and protease binding is prevented but still permits the formation of cancer cell-protease complexing. The effectiveness of the peptide binding with the serine proteases has profound affect on the intracellular events by unbalancing normal control mechanisms and key switches in the cascade of irreversible biochemical processes. As a result, there is a switching off of the production of $\alpha$1-PI and reduction in the controls to prevent cancer cell proliferation. Consequently, any proteolytic process, regulation by inhibition control, involved in the derepression of genes, e.g. those coding for biologically active proteins and those coding concomitantly for the cancer-associated proteases and their regulatory $\alpha$1-PI inhibitor along with the synthesis of cancer cell peptides, would in turn retain their proteolytic activity by the formation of the protease-peptide complexes instead of normal enzyme-$\alpha$1-PI complexes.

It has now been found that the balance can be restored by the administration of $\alpha$1-PI alone or in combination with other serine protease inhibitors and/or alpha 2-macroglobulin in an amount and for a time that proteolytic activity of protease inhibitors produced by the liver is sufficient.

In the case of virally produced cancer cells, $\alpha$1-PI has been found to have the dual role of killing on contact or inactivating the virus so as to inhibit viral proliferation as well as the virally induced cancer cells.

In the case of neoplastic mast cell tumors, $\alpha$1-PI acts on the inflammatory mediators released by the mast cells as well as preventing mast cell proliferation by inhibiting release of tumor necrosis factor-alpha (TNF-$\alpha$) which is believed to be one factor in causing the cellular proliferation. Injection to the site of tumors has been found to rapidly reduce tumor size.

Activated protease enzymes are essential in promoting cancer cells. Cancer cells bind with proteases to prevent their inhibition by high molecular weight serine protease inhibitors, particularly $\alpha$1-PI. Cancer cells produce peptides that are homologous to the enzyme binding sites of $\alpha$1-PI. These peptides contain two or three methionine residues.

The protective effect of these peptides in binding with serine proteases has a profound effect on the intracellular events by unbalancing normal control mechanisms and key switches in the cascade of irreversible biochemical processes. That is, $\alpha$1-PI is involved in the control of many intra- and extracellular physiological processes including degradative actions in cancer cell invasion, metastatic spread and neovascularization of tumors.

In the case of tumors or cancerous cells being on the skin, it has been found that topically applied $\alpha$1-PI to the site could be the mode of treatment.

Mucinous ovarian tumors contain a serine protease that is immunologically identical with trypsin which activates prourokinase. Therefore, it may participate in the protease cascade associated with invasive tumors. A cocktail of serine proteases would be the preferred treatment in this respect.

Alpha 1-antichymotrypsin is able to react with malignant fibrous histiocytosis so that a combination of alpha 1-antichymotrypsin with alpha i-antitrypsin would be a mode for treatment to prevent proliferation of the cancerous cells.

Mast cell tumors can be treated by a direct injection into or about the site of the tumor with 50 to 90 mg of the protease inhibitor weekly until the tumor has disappeared.

For multiple tumors or cancerous cells a daily infusion of 90 to 250 mg of the protease inhibitor may be required until disappearance of any cancerous cells or the tumors. Mass action of the protease inhibitors at the site of the tumors or cancerous cells provides the most beneficial effects by acting against the tumor and any tumor proteases or peptides which may be released.

The following examples further illustrate the practice of this invention, but are not intended to be limiting thereof. It will be appreciated that the actual amounts of the serine protease inhibitors to be administered will fall within the discretion of the attending physician and will be prescribed depending upon the stage of the disease.

EXAMPLES

The following examples were performed on animals in which prior administration of chemotherapeutic drugs did not produce a response. In example 1, the initial injection reduced the tumor in size by about 80%. PROLASTIN, marketed by Cutter Miles Laboratories, which is plasma derived alpha 1-antitrypsin was used in the example.

| Experiments of Tumor Treatment with Prolastin (Alpha-1-Antitrypsin) | Description of subject of the experiment | Cancer Type | Area of Cancer | Treatment | Results | Conclusions |
| --- | --- | --- | --- | --- | --- | --- |
| Example # 1 | Canine mixed-breed female 7-9 yrs. old | Mast cell tumor Grade II Neoplasm | left elbow | (i) Chemotherapy and radiation (interferon administered orally) (ii) Injected 60 mg. of Prolastin at site of tumor and injected 60 mg. of Prolastin again 2-3 weeks later | (i) had no measurable effect (ii) no evidence of recurrence of mast cell tumor significant reduction of tumor size | Injection of Prolastin at the site of a mast cell tumor reduces size of the tumor and prevents recurrence |
| Example # 2 | Canine mixed-breed female 6 yrs. old | Mast cell tumor | left hock (tarsal joint of hindleg) | excised part of tumor and treated remaining part of tumor by injecting 10 mg. Prolastin at site of tumor and again injecting 10 mg. of Prolastin 2-3 weeks later | no evidence of recurrence of mast cell tumor significant reduction of tumor size | Injection of Prolastin at the site of a mast cell tumor reduces size of the tumor and prevents recurrence |

What is claimed:

1. A method for treating mast cell tumors in dogs and humans which comprises administering to a dog or human an effective amount of alpha 1-antitrypsin.

2. The method of claim 1 wherein alpha 1-antitrypsin is administered in combination with another serine protease inhibitor.

3. The method of claim 2 wherein said other serine protease inhibitor is alpha 1-antichymotrypsin.

4. The method of claim 1 wherein alpha 1-antitrypsin is administered in combination with alpha 2-macroglobulin.

5. The method of claim 1 wherein said tumors are virally induced.

6. The method of claim 1 wherein alpha 1-antitrypsin is administered to the site of the tumor by injection.

* * * * *